(12) United States Patent
Fish et al.

(10) Patent No.: US 7,745,222 B2
(45) Date of Patent: Jun. 29, 2010

(54) AMYLOID BINDING ASSAYS

(75) Inventors: Kenneth Michael Fish, Clifton Park, NY (US); Cristina Tan Hehir, Niskayuna, NY (US); Michael Christopher Montalto, Albany, NY (US); Eric Dustin Agdeppa, Fairview, NJ (US)

(73) Assignee: General Electric Company, Niskayuna, NY (US)

( * ) Notice: Subject to any disclaimer, the term of this patent is extended or adjusted under 35 U.S.C. 154(b) by 803 days.

(21) Appl. No.: 11/580,493

(22) Filed: Oct. 13, 2006

(65) Prior Publication Data

US 2008/0274473 A1 Nov. 6, 2008

(51) Int. Cl.
*G01N 33/48* (2006.01)
(52) U.S. Cl. ........................................ 436/63
(58) Field of Classification Search ............... 436/63
See application file for complete search history.

(56) References Cited

U.S. PATENT DOCUMENTS

| | | | |
|---|---|---|---|
| 5,231,000 | A | 7/1993 | Majocha et al. |
| 5,750,349 | A | 5/1998 | Suzuki et al. |
| 5,811,310 | A | 9/1998 | Ghanbari et al. |
| 6,114,175 | A | 9/2000 | Klunk et al. |
| 6,133,259 | A | 10/2000 | Klunk et al. |
| 6,168,776 | B1 | 1/2001 | Klunk et al. |

FOREIGN PATENT DOCUMENTS

WO WO 2004/100998 11/2004

OTHER PUBLICATIONS

Das et al., BBA, 1571, 2002, 225-238.*
Merrifield, R. B., "Solid Phase Peptide Synthesis. I. The Synthesis of a Tetrapeptide", Rockefeller Institute, New York 21, N.Y., Jan. 31, 1963, pp. 2149-2154.
Li, Wen-Hong, Parigi, G., Fragai, M., Luchinat, C., and Meade, T. J., "Mechanistic Studies of a Calcium-Dependent MRI Contrast Agent", *Inorganic Chemistry*, vol. 41, No. 15, 2002, pp. 4018-4024.
Kuo, Y-M., et al., "Water-soluable Aβ (N-40, N-42) Oligomers in Normal and Alzheimer Disease Brains", *J. Of Biological Chemistry*, vol. 271, No. 8, Feb. 23, 1996, pp. 4077-4081.
Bahr, B.A., et al., "Amyloid βProtein Is Internalized Selectively by Hippocampal Field CA1 and Causes Neurons to Accumulate Amyloidogenic Carboxyterminal Fragments of the Amyloid Precursor Protein", *J of Comparative Neurology*, 397: pp. 139-147, 1998.

* cited by examiner

*Primary Examiner*—Maryam Monshipouri
(74) *Attorney, Agent, or Firm*—Eileen W. Gallagher

(57) ABSTRACT

Provided herein are amyloid-binding assays that simulate in situ brain conditions by combining binders with various A-beta species on mammalian brain tissue. In general the amyloid-binding assays comprise the steps of (a) contacting a mammalian brain tissue sample with at least one A-beta species; (b) applying a putative binder to the brain tissue sample; and (c) determining whether the putative binder binds to the A-beta species.

13 Claims, 5 Drawing Sheets

A

B

6E10

Thioflavin T

A    B

6E10    68B-3

A                                    B

6E10                              Thioflavin T

A B

6E10 68B-3

AMYLOID BINDING ASSAYS

FIELD OF THE INVENTION

The present invention relates to assays that may be employed to determine the ability of an agent to bind to one or more species of beta amyloid peptides.

BACKGROUND

The main histopathological characteristics of Alzheimer's disease ("AD") are the presence of neuritic plaques and tangles combined with associated inflammation in the brain. It is known that plaques are composed mainly of deposited (or insoluble in aqueous solution) fibrillar forms of the A-beta ("A-beta") peptide. The formation of fully fibrillar aggregated A-beta peptide is a complex process that is initiated by the cleavage of the amyloid precursor protein ("APP"). After cleavage of APP, the monomeric form of A-beta can associate with other monomers, presumably through hydrophobic interactions and/or domain swapping, to form dimers, trimers and higher order oligomers. Oligomers of A-beta can further associate to form protofibrils and eventual fibrils, which is the main constituent of neuritic plaques.

Soluble A-beta oligomers have also been implicated in neuronal dysfunction associated with AD. In fact, animal models suggest that simply lowering the amount of soluble A-beta peptide, without affecting the levels of A-beta in plaques, may be sufficient to improve cognitive function.

Presently, the only definitive method of AD diagnosis is postmortem examination of the brain or tissue for the presence of plaques and tangles. Currently, AD diagnosis is achieved using simple cognitive tests designed to test a patient's mental capacity such as, for example, the ADAS-cog (Alzheimer's disease assessment scale—cognitive subscale) or MMSE (Mini-mental state examination). The subjective nature and inherent patient variability is a major shortcoming of diagnosing AD by such means. The inability to diagnose AD in a living patient presents a formidable challenge for pharmaceutical companies that aim to test putative therapeutics to slow or halt AD pathogenesis by acting on one or more species of A-beta. Because A-beta binders are needed for diagnostic and/or therapeutic applications, significant needs exist for methods of assaying the ability of agents to bind to various species of A-beta.

BRIEF DESCRIPTION

Provided herein are various methods for determining the ability of a putative binder to bind an A-beta species comprising the steps of: (a) contacting a mammalian brain tissue sample with at least one A-beta species; (b) applying a putative binder to the brain tissue sample; and (c) determining whether the putative binder binds to the A-beta species.

In some embodiments, the disclosed methods provide additional control steps wherein each of steps (a)-(c) are repeated using a validated binder in place of the putative binder to provide a positive control. Thus, for the positive control variant, steps (a)-(c) may be repeated using a validated binder in place of the putative binder. Likewise, for the negative control variant, steps (a)-(c) may be repeated using a validated nonbinder in place of the putative binder. For either positive control or negative control variations the additional control steps (a)-(c) may be performed either in parallel or in tandem with the assay for the putative binder. In all embodiments including one or more control the methods may include the additional step of determining the relative binding of the putative binder and the validated binder or the validated nonbinder.

The step of applying an A-beta species to mammalian brain tissue may occur while the brain tissue is present in the animal or after the brain tissue has been removed from the animal. Accordingly, the contacting step may include introducing the at least one A-beta species into an intact mammalian brain before the applying step. In such embodiments, the A-beta species may introduced into a mammalian brain by any art recognized method (e.g., intracranial injection or intravascular injection). In alternative embodiments, the brain tissue is isolated from an intact brain prior to the applying step.

In all embodiments, the brain tissue sample may be process according to standard pathology methods, for example a tissue section of about 10 microns to about 30 microns thick, applying a preserving agent to the brain tissue sample, and/or embedding the sample in a wax-type agent (e.g., paraffin). The disclosed methods may also include one or more washing steps following either or both the contacting and applying steps.

The A-beta species applied to the brain tissue may be varied according the user's purposes and may substantially comprises a naturally occurring or synthetic monomers or multimers of A-beta (e.g., soluble or insoluble A-beta). Although, the amount of the A-beta species applied to the brain tissue sample may be varied, in some preferred embodiments the final a concentration of about 0.1 pM to about 0.1 nM.

The type of binder (putative, validated binder or validated non-binder) may comprise and form of binder (e.g., small molecules, antibodies, or antibody fragments). In some preferred embodiments, the validated binder may comprise a small molecule that preferentially binds to soluble A-beta relative to insoluble A-beta (e.g., benzofuran derivates such as 68b-3). In some embodiments the A-beta species is soluble A-beta and the validated nonbinder comprises Thioflavin S.

The determining binding step may entail any art recognized methods of determine binding in a tissue sample, for example optically observing the binding using fluorescence microscopy or radiographic imaging. Where the binder has an inherent ability to general a measurable signal when present in a sample (e.g. fluoresces or generates a radioactive signal), no additional agents are required for the determining binding step. If, however, the binder does not have the ability to generate signal, the disclosed methods additional steps of applying a signal generator to facilitate the binding determination step. Such an additional step may employ, for example, a labeled antibody that recognizes the binder.

DETAILED DESCRIPTION

Figure 1:
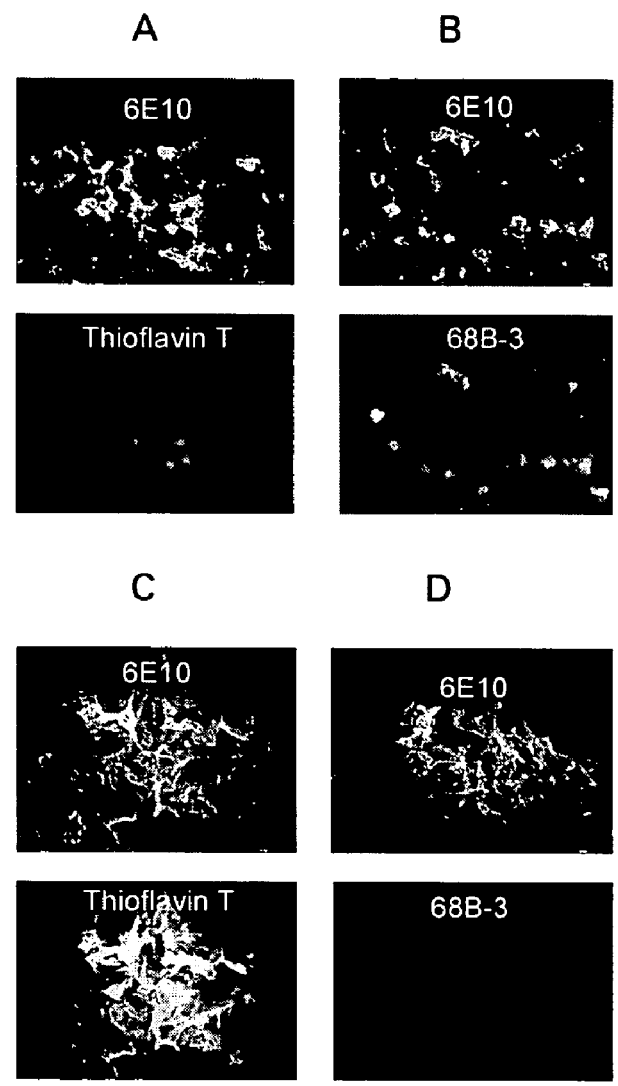
FIG. 1A-1D are side-by-side presentations of FIGS. 2-5, in which several different putative or validated A-beta binders have been assayed using synthetic or naturally occurring A-beta species in the context of mammalian brain tissue.
Figure 2:
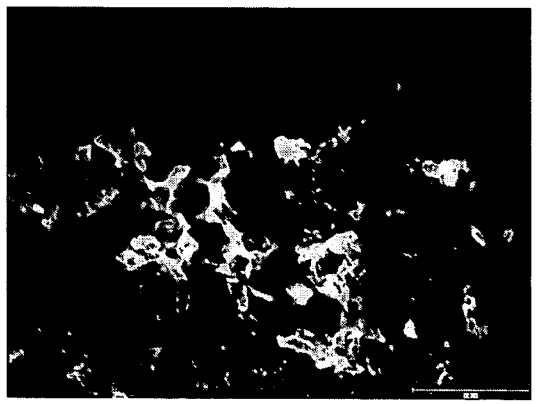
FIG. 2A-2B shows anti-A-beta primary antibody 6E10 and Thioflavin T bound to soluble oligomeric A-beta.
Figure 2:
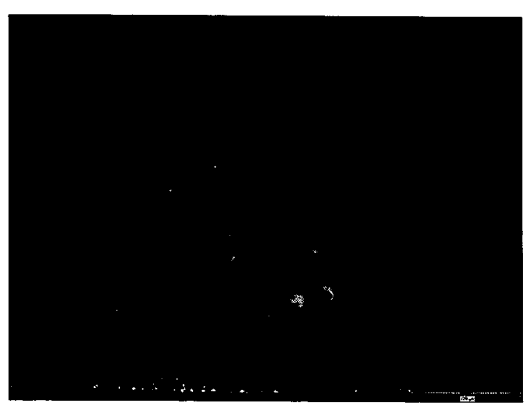
Figure 3:
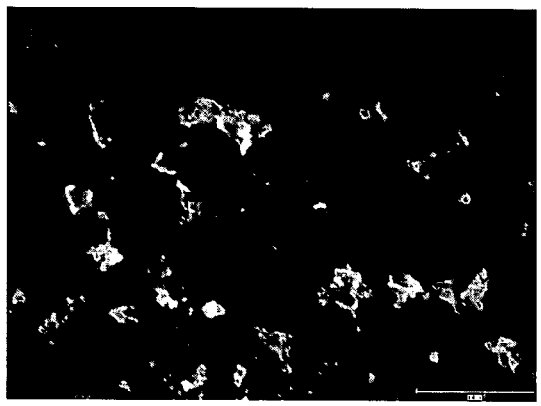
FIG. 3A-3B show 6E10 and 68B-3 bound to soluble oligomeric A-beta.
Figure 3:
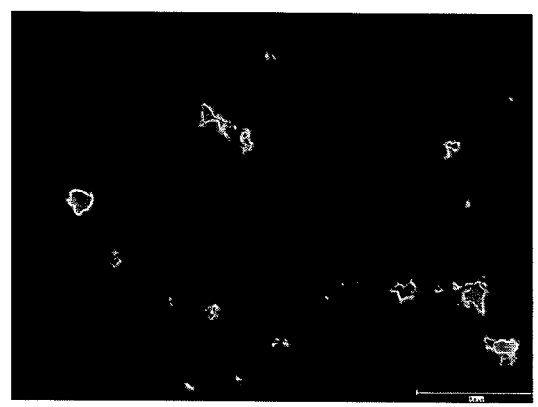
Figure 4:
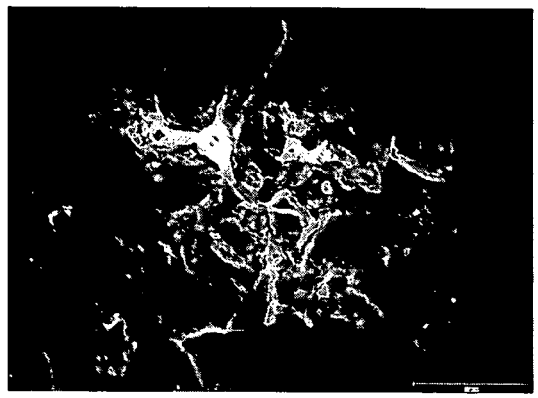
FIG. 4A-4B show 6E10 and Thioflavin T bound to A-beta fibrils.
Figure 4:
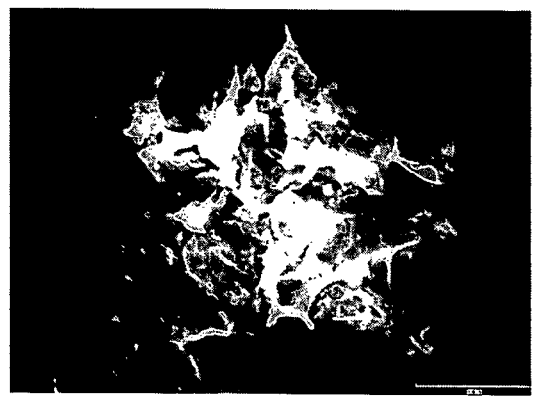
Figure 5:
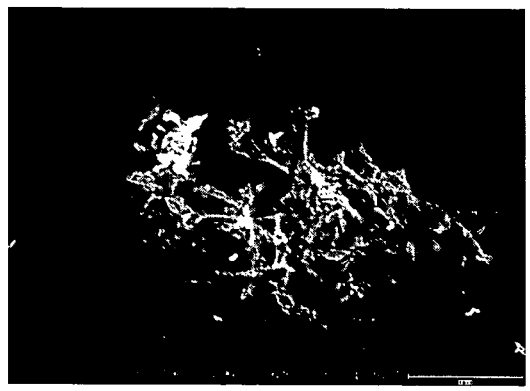
FIG. 5A-5B show 6E10 and 68B-3 to bound to fibrillar A-beta fibrils.
Figure 5:

The following detailed description is exemplary and not intended to limit the invention of the application and uses of the invention. Furthermore, there is no intention to be limited by any theory presented in the preceding background of the invention of the following detailed description of the drawings.

To more clearly and concisely describe and point out the subject matter of the claimed invention, the following definitions are provided for specific terms that are used in the following description and the claims appended hereto.

As used herein, the term "assay" generally refers to qualitative or quantitative determinations of the ability of a substance to bind or otherwise affect various species of A-beta.

As used herein, the term "antibody" refers to an immunoglobulin that specifically binds to and is thereby defined as complementary with a particular spatial and polar organization of another molecule. Antibodies useful in present invention may be monoclonal or polyclonal and may be prepared by art-recognized techniques such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies of the various classes and isotypes (e.g., IgA, IgD, IgE, IgG1, IgG2a, IgG2b and IgG3, IgM) may also include a complete immunoglobulin or functional fragments. In addition, aggregates, polymers, and conjugates of immunoglobulins or their fragments can be used where appropriate so long as an appropriate binding affinity for a particular molecule is maintained.

As used herein, the term "A-beta species" generally refers to the various forms of A-beta-derived polypeptide identified by SEQ ID: 1. In general, A-beta may comprise amyloid polypeptides of varying length, various aggregation states, and/or solubility. The term "A-beta species" is intended to encompass A-beta species of varying polypeptide lengths. Thus, A-beta species may include various forms of A-beta amino acid residues 1 through 43 of the full length A-beta peptide shown in SEQ. ID NO:1. Alternatively, the A-beta species may consist essentially of: residues 1-42 of the full length A-beta peptide, residues 1 through 40 of the full length A-beta peptide, residues 1-39 of the full length A-beta peptide, residues 1-38 of the full length A-beta peptide, residues 3-40 of the full length A-beta peptide, residues 3-42 of the full length A-beta peptide, residues 11-40 of the full length A-beta peptide, residues 11-42 of the full length A-beta peptide, residues 17-40 of the full length A-beta peptide, and residues 17-42 of the full length A-beta peptide.

The general term A-beta species also encompasses various forms of A-beta in several aggregation states (e.g., monomeric, soluble oligomers, or insoluble oligomeric). Because a variety of factors may affect which species of A-beta is found in solution, the aggregation state of the A-beta species may be selected according to the user's purposes by altering the A-beta polypeptide length, increasing or decreasing the concentration of A-beta present in a given aliquot of A-beta species, increasing or decreasing the temperature, pH, salt levels and metal content (e.g., $Zn^{2+}$ $Cu^{2+}$, etc.) of the given aliquot of A-beta species.

Various forms of soluble or insoluble A-beta species (regardless of the length of the polypeptide or the association state) may be derived from a variety of mammalian tissue sources, including but not limited to, brain tissue, cerebrospinal fluid, or blood serum. Alternatively, the A-beta species may be synthesized using art-recognized techniques such as protein expression systems or peptide synthesizers.

Although useful compositions may substantially comprise a particular species of identified A-beta (e.g., 1-42), they may also comprise an insubstantial amount of another species (e.g., of shorter or longer portions of the A-beta polypeptide).

As used herein, the term "binder" refers to a substance having a sufficiently strong binding constant to detectably bind to A-beta. Binders may be either validated binders (i.e., agents known to bind to one or more amyloid species) or putative binders (i.e., agents that binding ability to an amyloid species has not been determined). In the present methods, the putative binders are the subject of the assay, validated binders may be used as positive controls, and validated non-binders may be used as negative controls. Furthermore, validated binders with known binding affinities for one or more A-beta species may be used as the competition in competition assays employing the methods disclosed herein.

As used herein the term "complexed" generally refers to the aggregation state of A-beta species in solution (e.g., monomeric or multimeric aggregates of the A-beta polypeptide). Thus, the terms "complex" and "oligomer," as used herein, refer to the polypeptides in the associated or bound state. And, the term "monomer" refers to a single peptide chain of A-beta.

As used herein, the terms "fibrils" and "fibrillar" generally refer to A-beta preparations with largely beta-sheet content that are insoluble aggregates. Fibrils bind Congo Red and Thioflavin T dyes and cause these dyes to produce fluorescence signal. Fibril preparations preferentially comprise substantially fibrillar A-beta, but they may also comprise unsubstantial amounts of globular aggregates.

As used herein, the term "healthy mammalian brain tissue" refers to mammalian brain tissue unaffected by an amyloid-associated disease (e.g., Alzheimer's disease).

As used herein, the term "soluble oligomers" generally refers to complexed A-beta polypeptides short chain of monomers derived from the A-beta polypeptide, preferentially less than 25 monomers in length, but may be 100 monomers in length. For example, although the precise oligomer stoichiometry need not be determined, oligomer preparations preferentially comprise substantially soluble A-beta oligomers, but will also comprise unsubstantial amounts of large globular aggregates.

As used herein, the term "signal generator" encompasses a substance that is capable of being detected by any method (e.g., optical detection or radiography) in the course of an assay. Examples of signal generators include, but are not limited to, fluorophores (e.g., cyanine dyes), radioisotopes or spin labels.

As used herein, the term "small molecule" refers to an organic molecule, either naturally occurring or synthetic, that has a molecular weight less than about 5000 daltons, and preferentially in the range of about 200 to about 2000 daltons.

As used herein with regard to the A-beta species, the term "soluble" refers to nonaggregated A-beta peptides. Soluble A-beta oligomers are relatively stable and exhibit structural and functional characteristics that are distinct from the fibrillar amyloidogenic form of A-beta. In general the aggregation status of A-beta peptides may be broken into three categories: (1) micelles; (2) protofibrils; and (3) fibrils. The aggregation state of A-beta species may be determined using the techniques set out in Goldsbury et. al, J Struct Biol.; June; 130(2-3):352-62, (2000), in which samples are classified by the amount of β strands in undisturbed solution (pH 7.4 at 37° C.) by CD. Under these conditions (1) micelles demonstrate 0% β strands; (2) protofibrils demonstrate about 76% β strands; and (3) fibrils demonstrate 100% β strands. Soluble A-beta species for the assays of the invention contain only insubstantial amounts of protofibrils and fibrils.

As used herein, the term "preferentially binds" refers to the specific recognition of one of two different molecules for the other compared to substantially less recognition of other molecules. Thus, an agent that specifically binds a target molecule demonstrates affinities at least five-fold, and preferentially 10-fold to 100-fold affinities greater than non-binders. Examples of specific binding include antibody-antigen interactions, enzyme-substrate interactions, polynucleotide interactions, and so forth.

An agent exhibits "specific binding" if it reacts or associates more frequently, more rapidly, with greater duration and/or with greater affinity with a particular target than it does with alternative cells or substances. The specific binders associate with one or more A-beta species with high affinity for example, an affinity constant of at least $10^7 M^{-1}$, preferably between $10^8 M^{-1}$ and $10^{10} M^{-1}$, or about $10^9 M^{-1}$.

As used herein, the term "species-specific binder" refers to any binder that preferentially attaches to one particular species of A-beta (e.g., soluble A-beta) relative to other species of A-beta (e.g., fibrillar A-beta).

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

DETAILED DESCRIPTION

The present disclosure relates to amyloid binding assays comprising the steps of obtaining mammalian brain tissue, exposing the brain tissue to a predetermined amount of A-beta species, applying a binder to the brain tissue, observing binding of the binder to the A-beta species. Introducing a binder onto one or more A-beta species in the context of brain tissue simulates in situ conditions, permitting enhanced reliability to the assays disclosed herein relative to assays that combine the a binder with A-beta in some other substrate (e.g., a plastic tube).

In an aspect of the assays, obtaining a mammalian brain tissue comprises obtaining naïve rat brains, and splicing the brain to sections about 10 microns thick. Any mammalian brain, including human, may be spliced, sectioned, and used. Each section may be frozen after sectioning or used immediately after the sectioning step. Furthermore, each section maybe fixed using fixing agents (e.g., formalin in a PBS), and optionally embedded (e.g., in paraffin).

In another aspect of the assays, exposing the brain tissue to a predetermined amount of A-beta species comprises generating A-beta species and, applying a predetermined amount of A-beta species to sections of mammalian brain tissue. Alternatively, the exposing the brain tissue to a predetermined amount of A-beta step may be performed prior to obtaining or isolating the mammalian brain tissue. Thus, a predetermined amount of A-beta may be injected into a mammal intracranially or intravenously, and waiting a sufficient amount of time for the A-beta species to migrate to the brain tissue before isolating the tissue sample.

Providing the A-beta species may comprise selecting and preparing a species of A-beta to be applied to the brain tissue. In some aspects of the assays, soluble A-beta oligomers is preferred while in other aspects of the assays fibrillar amyloidogenic species of A-beta is preferred. Preparing soluble A-beta oligomers may comprise using human A-beta polypeptide 1-42, solubilizing it with 1,1,1,3,3,3 hexafluoro-2-propanol (HFIP) and drying it to a film under a vacuum, which may again be dissolved in HFIP. If storage is desirable, a temperature of about 20° C. is preferred. Prior to use, dried film may be dissolved in an appropriate amount of a solvent (e.g., DMSO) and the volume adjusted with water. Although the final concentration of a solution containing the A-beta species may be varied according to the purpose of the user, a final concentration to about 200 uM is convenient because the volume of liquid introduced onto the tissue sample may be kept small (e.g., about 1 μL to about 10 μL). Small volumes are particularly useful in embodiments in which the A-beta species is introduced into the brain of an animal.

The species of A-beta applied to the brain tissue section may be varied according to the user's purposes. Thus, if the user is interested in determining whether an agent binds to A-beta fibrils, A-beta fibrils may be applied to brain tissue sections. Preparing A-beta fibrils may comprise using lyophilized human A-beta 1-40 polypeptide and solubilizing it with HFIP to make dry film using the same methods described above to make soluble A-beta oligomers. This resulting film will be diluted with distilled water to a concentration of about 6 mg/mL, and then diluted again with PBS to about pH 7.4 down to about 1 mg/mL. The resulting solution may be incubated at 37° C. and gently agitated (e.g., orbital shaker at 200 RPM) for an extended period of time (e.g., 4 days or more).

Preparing A-beta monomers may comprise dissolving A-beta 1-42 (SEQ. ID NO. 1) polypeptide in HFIP to a concentration of about 100 nM and used immediately after HFIP solubilization. Alternatively, A-Beta 1-40 may be used instead of 1-42, and may be dissolved first in DMSO followed by dilution in aqueous solution (e.g., PBS), then used immediately. The final concentration of DMSO may be between about 1 to about 2%. The A-beta oligomers and monomers may be centrifuged at about 10,000 rpm for about 5 minutes to remove precipitated peptides. Centrifugation may not always be necessary.

Regarding ex vivo application of A-beta, preferred amounts of A-beta solution applied onto brain tissue are generally about 1 μL from a 100 μM stock solution. The amount of A-beta applied to the brain tissue may vary according to the desired level of sensitivity selected by the user. Thus, amounts of A-beta ranging from about 100 nM to about 100 μM A-beta may be used. The A-beta species may be applied to specific target brain tissue by obtaining the tissue from a predetermined region of interest or applying the A-beta directly to a predetermined region of interest. Thus, the A-beta species may be directed to the hippocampus because of its known relation to amyloidogenic disease. Alternatively, any other part of the medial temporal lobe, the frontal lobe, or the occipital lobe may be employed in various aspects of these assays.

Volumes in the range of about 1 to about 50 μL are preferred in tissue section embodiments and volumes in the range of about 1 to about 5 μL are preferred in embodiments where the A-beta species is introduced into an animal (e.g., intracranial injection or intravascular injection).

With regards to in vivo application of A-beta, in one aspect of the assays injecting up to 10 µl intracranially. Enough solution should be injected so as to obtain viable imaging results. In a different aspect of the assays, injecting intravenously in the tail vein up to 200 µl for mice, or up to 500 µl for rats. When dealing with a rodent as a test subject, injections may occur in the tail or in any known vein. Again, enough solution should be injected so that a viable amount of A-beta species crosses the blood brain barrier. Solution amount may vary with A-beta concentration, rodent size, or pathological differences between them.

Subsequent to application, incubating for about 2 hours at about 37° C., the sample may be washed with a buffer (e.g., PBS), and incubated again at similar lengths of time and temperatures with a blocking buffer (e.g., 10% normal goat serum in 3% BSA in PBS).

In one aspect of the assays, applying a binder to the brain tissue may comprise a binder that has a binding function and a signal generating function in a single entity—for instance, agents that bind to soluble A-beta and there are imaging agents and dyes that bind exclusively to insoluble deposits of A-beta or senile plaques. Small molecules that specifically bind to insoluble A-beta deposits may include, for example, small molecular weight molecules, such as Congo red, Chrysamine G, methoxy-X04, TZDM, [$^{11}$C]6, IMSB, Thioflavin(e) S and T, TZDM, 1-BTA, benzathiozole derivatives, [$^{125}$I]3, BSB, IMSB, styrylbenzene-derivatives, IBOX, benzoxazole derivatives, IMPY, pyridine derivatives, DDNP, FDDNP, FENE, dialkylaminonaphthyl derivatives, benzofuran derivatives, and derivatives thereof as described in U.S. Pat. Nos. 6,133,259; 6,168,776; 6,114,175.

Also useful in the disclosed methods are peptides have also been developed as imaging agents for insoluble deposits of A-beta and senile plaques. The sequence specific peptides that have been labeled for the purpose of imaging insoluble A-beta includes the labeled A-beta peptide itself, putrescine-gadolinium-A-beta peptide, radiolabeled A-beta, [$^{111}$In]A-beta, [$^{125}$I]A-beta, A-beta labeled with gamma emitting radioisotopes, A-beta-DTPA derivatives, radiolabeled putrescine, KVLFF-based ligands and derivatives thereof.

In another aspect of the assays, the binding function and the signal generating function are performed by two or more distinct entities (e.g., anti-A-beta primary antibody and a secondary fluorescence antibody). Antibodies specific for soluble and insoluble A-beta can be prepared against a suitable antigen or hapten comprising the desired target epitope, such as the junction region consisting of amino acid residues 13-26 and/or the carboxy terminus consisting of amino acid residues 33-42 of A-beta. One suitable antibody to soluble A-beta is disclosed in Kayed, et al., Science, vol. 300, page 486, Apr. 18, 2003.

Synthetic peptides can also be prepared by conventional solid phase techniques, coupled to a suitable immunogen, and used to prepare antisera or monoclonal antibodies by conventional techniques. Suitable peptide haptens typically will comprise at least five contiguous residues within A-beta and can include more than six residues. Synthetic polypeptide haptens can be produced by the Merrifield solid-phase synthesis technique in which amino acids are sequentially added to a growing chain (Merrifield (1963) J. Am. Chem. Soc. 85:2149-2156). Other suitable antibodies include, for example, those of U.S. Pat. Nos. 5,811,310; 5,750,349; and 5,231,000, R1282, 21F12, 3D6, FCA3542, and monoclonal and polyclonal antibodies for A-beta 1-40, 1-42 and other isoforms.

Certain imaging agents have been developed that can report on the specific presence of a target molecule without binding to that molecule. In such instances the imaging agents are considered "activatable" because their signal is activated or unactivated based on the presence of a specific target molecule. Examples of such agents have been used for MRI and optical imaging (Li W H, Parigi G, Fragai M, Luchinat C, Meade T J, Inorg Chem 2002 Jul. 29; 41(15):4018-24)(Louie A Y, Huber M M, Ahrens E T, Rothbacher U, Moats R, Jacobs R E, Fraser S E, Meade T J. Nat Biotechnol 2000 March; 18(3):321-5) (Weissleder R, Tung C H, Mahmood U, Bogdanov A Jr Nat Biotechnol 1999 April; 17(4):375-8).

Regarding imaging, wide-field fluorescence microscopy used to image both fluorophores and immunostains (e.g., 6E10). A radiolabel must have a type of decay that is detectable by the available imaging modality. Suitable radioisotopes are well known to those skilled in the art and include beta-emitters, gamma-emitters, positron-emitters, and x-ray emitters. Suitable radioisotopes include $^{3}$H, $^{11}$C, $^{14}$C, $^{18}$F, $^{32}$P, $^{35}$S, $^{123}$I, $^{125}$I, $^{131}$I, $^{51}$Cr, $^{36}$Cl, $^{57}$Co, $^{59}$Fe, $^{75}$Se, and $^{152}$Eu. Isotopes of halogens (such as chlorine, fluorine, bromine and iodine), and metals including technetium, yttrium, rhenium, and indium are also useful labels. Typical examples of metallic ions that can be bound are $^{99m}$Tc, $^{123}$I, $^{111}$In, $^{131}$I, $^{97}$Ru, $^{67}$Cu, $^{67}$Ga, $^{125}$I, $^{68}$Ga, $^{72}$As, $^{89}$Zr, and $^{201}$Tl. For use with the present disclosure, radiolabels can be prepared using standard radiolabeling procedures well known to those skilled in the art.

In another aspect of the invention, calculating the sum of pixel intensity for each individual image, the whole field view may be selected using analysis subroutines with Leica FW 400 image software package, although other techniques to sum pixel intensity may be used as well.

EXAMPLES

Practice of the invention will be still more fully understood from the following examples, which are presented herein for illustration only and should not be construed as limiting the invention in any way.

Example 1

Preparation of Brain Tissue

In one embodiment, sections of Sprauge-Dawley naïve rat brain (Taconic) 10 microns in thickness were fixed with 10% formalin in phosphate buffered saline (PBS). Each section of the rat brain was then embedded in paraffin, an optional step that increases the shelf life of the sample.

Example 2

Preparation and Application of A-Beta Species

Soluble A-beta oligomer formation. 1 mg of human beta-amyloid 1-42 (H-5642, Bachem) and 500 uL of 1,1,1,3,3,3 hexafluoro-2-propanol (HFIP) (Aldrich) were chilled in separate bottles on ice for 30 minutes. Cold beta-amyloid 1-42 was solubilized with cold HFIP. The mixture was incubated for 1 hr at room temperature until it turned clear. The resulting solution was then dried to a film under vacuum. The film was dissolved again in cold HFIP and incubated another 1 hr at room temperature. The resulting solution was separated into aliquots in several microcentrifuge tubes. HFIP was removed under vacuum, and the films were stored at −20° C. until use. To prepare soluble oligomer, the film was dissolved in appropriate amount of dry DMSO (Sigma), and Ham's F12 media (Biosource) or PBS (Sigma, D8537) was added and incubated at 4° C. for 24 hours (final concentration of 200 uM or 0.9 mg/mL beta-amyloid in 2% DMSO).

A-beta fibril preparation. Unless otherwise indicated, all numbers expressing quantities of ingredients, properties Lyophilized human A-beta 1-40 peptide (H01194, Bachem) was solubilized with (HFIP) to produce a dry, clear film following the aforementioned method to make dry films of A-beta 1-42. The clear film of A-beta 1-40 was diluted with distilled water to achieve a 6-mg/mL concentration. If the resulting solutions had a cloudy appearance, then the solution was placed in an ultrasonic bath until the solution became clear. The clear solution was diluted to 1 mg/mL with PBS, pH 7.4 to obtain a final concentration of 1 mg/mL A-beta 1-40 then incubated at 37° C. on an orbital shaker at 200 RPM for 4 days.

Unless otherwise indicated, all numbers expressing quantities of ingredients, properties A-beta 1-42 was dissolved in HFIP (0.5 mg/mL) and was used immediately after HFIP solubilization. The 68b-3 binder a validates preferential binder for soluble A-beta with the following formula:

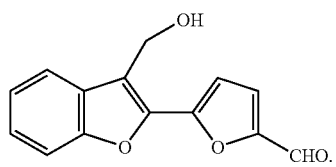

With reference to binder 68b-3, the monomer concentrations used were 100 μM in HFIP 1 ul of A-beta solution was applied onto the brain tissue sections targeting the hippocampus and incubated in a humidified chamber for two hours at 37° C. The slides were washed with PBS three times then incubated with blocking buffer consisting of 10% normal goat serum in 3% BSA in PBS.

Example 3

Binder and Signal Generator Preparation

Some of the examples that follow the binding function and signal generation function are served by a single entity, in other examples the binding function and the signal generating function are performed by two (or more) distinct entities. The presence of A-beta species was verified using a sandwich assay with anti-A-beta primary antibody and a secondary fluorescence antibody. In an alternate approach, the presence of A-beta was verified using small molecules that auto-fluoresce upon binding with A-beta.

For the sandwich assay approach 100 μL of $1/250^{th}$ dilution of anti-A-beta antibody, (Signet) was applied to the tissue. The tissue was then incubated for 1.5 hours at room temperature, or in an alternative approach, for 45 minutes at 37° C. Next, a $1/100^{th}$ dilution of the secondary antibody Alexa Flour 594-goat antimouse IgG (Molecular Probes) was prepared in PBS and 100 μl was applied to the slides, which were then incubated at room temperature for 1.5 hours. The slides were then washed three times in PBS and cover slipped with a mounting medium (AntiFade Gold, Molecular Probes) and incubated at 4° C. at least 4-6 hours before imaging.

When fluorescent small molecules 68B-3, and Thioflavin S were used, both binders and signal generating moieties were present in a single component. These small molecules were prepared using 1 mM stock solutions of each in 50% ethanol. Each solution was then diluted to 50 μM in blocking buffer. 100 μL of each solution was then added to the slides containing 100 μL of 6E10. The 6E10 antibody was not removed prior to addition of these solutions. The slides were then incubated in a humidified chamber for one hour at room temperature, then washed three times with PBS.

Example 4

Imaging and Analysis

Microscopic examination was performed using a Leica (Leica Microsystems Inc, Bannockburn Ill.) wide-field fluorescence microscope. As shown below in Table 1, filter cube A (Band Pass 340-380 nm with a 400 nm dichroic mirror and a long pass 400 nm suppression filter) was used for a 68B-3, filter cube E4 (Band pass 436 nm with 455 dichroic mirror and a long pass 470 nm suppression filter) was used for Thioflavin T, and TX2 (Band pass 520-600 nm with a 595 nm dichroic mirror and a 645/75 band pass suppression filter) was used for 6E10 immunostaining.

TABLE 1

| CUBE | Band Pass (nm) | Dichroic Mirror (nm) | Long Pass Suppression Filter (nm) | Band Pass Suppression Filter |
|---|---|---|---|---|
| Filter Cube A | 340-380 | 400 | 400 | NA |
| TX2 | 520-600 | 595 | NA | 645/75 |
| E4 | 436 | 455 | 470 | NA |

The fluorescent images were quantified by calculating the sum of pixel intensity of the immunofluorescence for each amyloid species. To sum the pixel intensity for each individual image, the whole field of view was selected using the analysis sub-routines with the Leica FW 400 image software package.

Example 5

Control Step

The assays of the invention may comprise steps to establish baseline values or compare the binding capabilities of a putative binder or validated binder (i.e., an agent possessing a known binding affinity for a particular species of A-beta) with an agent under consideration. Thus, in addition to the steps described in each of the above examples, one or more additional samples comprising a validated binder and/or a validated nonbinder may be prepared in parallel or in tandem and processed along with the primary sample.

Thus, for example, in one sample, the brain tissue section maybe processed as above including the step of overlaying the brain tissue sample with one or more A-beta species followed by the application of a validated binder and measuring the binding to establish a baseline or control value. Using a validated binder the additional sample or samples may provide negative controls. Conversely, where the known binder has a high affinity for the particular A-beta species being assayed, the additional sample or samples may provide positive controls.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

We claim:

1. A method of identifying a putative binder to bind an A-beta-derived polypeptide having SEQ ID: 1 comprising the steps of:
  (a) contacting a mammalian brain tissue sample with at least one A-beta-derived polypeptide having SEQ ID: 1;
  (b) applying a putative binder to the brain tissue sample; and
  (c) determining whether the putative binder binds to the A-beta-derived polypeptide having SEQ ID: 1.

2. The method of claim 1, wherein the contacting step includes introducing the at least one A-beta-derived polypeptide having SEQ ID: 1 into an intact mammalian brain before the applying step.

3. The method of claim 1, wherein the at least one A-beta-derived polypeptide having SEQ ID: 1 is introduced into a mammalian brain by intracranial injection or intravascular injection.

4. The method of claim 1, further comprising the step of isolating a brain tissue sample from an intact brain prior to the applying step.

5. The method of claim 1, further comprising the step of creating a tissue section of about 10 microns to about 30 microns thick.

6. The method of claim 1, further comprising the step of applying a preserving agent to the brain tissue sample.

7. The method of claim 1, further comprising one or more washing steps following either or both the contacting and applying steps.

8. The method of claim 1, wherein the A-beta-derived polypeptide having SEQ ID: 1 substantially comprises a naturally occurring or synthetic monomers or multimers of A-beta.

9. The method of claim 1, wherein the amount of the A-beta-derived polypeptide having SEQ ID: 1 applied to the brain tissue sample is a concentration of about 0.1 pM to about 0.1 nM.

10. The method of claim 1, wherein the A-beta-derived polypeptide having SEQ ID: 1 spies is selected from soluble or insoluble A-beta.

11. The method of claim 1, wherein the binder comprises an antibody or a functional antibody fragment.

12. The method of claim 1, further comprising the step of applying at least one signal generator capable of binding to the binder to the brain tissue prior to the observing step.

13. The method of claim 1, wherein the observing step comprises observing the binding using fluorescence microscopy or radiographic imaging.

* * * * *

UNITED STATES PATENT AND TRADEMARK OFFICE
CERTIFICATE OF CORRECTION

PATENT NO. : 7,745,222 B2
APPLICATION NO. : 11/580493
DATED : June 29, 2010
INVENTOR(S) : Fish et al.

It is certified that error appears in the above-identified patent and that said Letters Patent is hereby corrected as shown below:

In Column 2, Line 61, delete "shows" and insert -- show --, therefor.

In Column 11, under "SEQUENCE LISTING", Line 5, delete "Homo sapiens" and insert -- mammalian --, therefor.

In Column 12, Line 36, in Claim 10, after "1" delete "spies".

Signed and Sealed this

Twenty-fourth Day of August, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 43
<212> TYPE: PRT
<213> ORGANISM: Homo sapiens

<400> SEQUENCE: 1

Asp Ala Glu Phe Arg His Asp Ser Gly Tyr Glu Val His His Asn Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40